(12) United States Patent
Hogan et al.

(10) Patent No.: US 10,920,274 B2
(45) Date of Patent: Feb. 16, 2021

(54) NUCLEIC ACID COATED SUBMICRON PARTICLES FOR AUTHENTICATION

(71) Applicant: APDN (B.V.I.) Inc., Tortola (VG)

(72) Inventors: Michael E. Hogan, Stony Brook, NY (US); Lawrence Jung, Dix Hills, NY (US); Nicole Richter, Port Jefferson, NY (US); Yuhua Sun, Stony Brook, NY (US); Maciej Szczepanik, Mount Sinai, NY (US)

(73) Assignee: APDN (B.V.I.) Inc., Tortola (VG)

( * ) Notice: Subject to any disclaimer, the term of this patent is extended or adjusted under 35 U.S.C. 154(b) by 283 days.

(21) Appl. No.: 15/890,541

(22) Filed: Feb. 7, 2018

(65) Prior Publication Data

US 2018/0237854 A1 Aug. 23, 2018

Related U.S. Application Data

(60) Provisional application No. 62/461,312, filed on Feb. 21, 2017.

(51) Int. Cl.
*C12Q 1/6876* (2018.01)
*C12Q 1/68* (2018.01)

(52) U.S. Cl.
CPC ............ *C12Q 1/6876* (2013.01); *C12Q 1/68* (2013.01)

(58) Field of Classification Search
None
See application file for complete search history.

(56) References Cited

U.S. PATENT DOCUMENTS

| | | |
|---|---|---|
| 4,183,989 A | 1/1980 | Tooth |
| 4,278,557 A | 7/1981 | Elwell, Jr. |
| 4,454,171 A | 6/1984 | Diggle, Jr. et al. |
| 4,548,955 A | 10/1985 | Okahata et al. |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,861,620 A | 8/1989 | Azuma et al. |
| 4,965,188 A | 10/1990 | Mullis et al. |
| 5,047,519 A | 9/1991 | Hobbs, Jr. et al. |
| 5,075,216 A | 12/1991 | Innis et al. |
| 5,089,691 A | 2/1992 | Morisaki et al. |
| 5,132,242 A | 7/1992 | Cheung |
| 5,139,812 A | 8/1992 | Lebacq |
| 5,151,507 A | 9/1992 | Hobbs, Jr. et al. |
| 5,156,765 A | 10/1992 | Smrt et al. |
| 5,176,203 A | 1/1993 | Larzul |
| 5,270,183 A | 12/1993 | Corbett et al. |
| 5,415,839 A | 5/1995 | Zaun et al. |
| 5,429,952 A | 7/1995 | Garner et al. |
| 5,451,505 A | 9/1995 | Dollinger |
| 5,498,283 A | 3/1996 | Botros et al. |
| 5,508,197 A | 4/1996 | Hansen et al. |
| 5,595,871 A | 1/1997 | DelVecchio et al. |
| 5,599,578 A | 2/1997 | Butland |
| 5,602,381 A | 2/1997 | Hoshino et al. |
| 5,639,603 A | 6/1997 | Dower et al. |
| 5,643,728 A | 7/1997 | Slater et al. |
| 5,736,314 A | 4/1998 | Hayes et al. |
| 5,763,176 A | 6/1998 | Slater et al. |
| 5,776,713 A | 7/1998 | Garner et al. |
| 5,849,208 A | 12/1998 | Hayes et al. |
| 5,866,336 A | 2/1999 | Nazarenko et al. |
| 5,912,257 A | 6/1999 | Prasad et al. |
| 5,942,444 A | 8/1999 | Rittenburg et al. |
| 5,956,172 A | 9/1999 | Downing |
| 5,977,436 A | 11/1999 | Thomas et al. |
| 5,989,823 A | 11/1999 | Jayasena et al. |
| 6,013,789 A | 1/2000 | Rampal |
| 6,030,657 A | 2/2000 | Butland et al. |
| 6,033,880 A | 3/2000 | Haff et al. |
| 6,057,370 A | 5/2000 | Weiland et al. |
| 6,127,120 A | 10/2000 | Graham et al. |
| 6,132,996 A | 10/2000 | Hunicke-Smith |
| 6,140,075 A | 10/2000 | Russell et al. |
| 6,169,174 B1 | 1/2001 | Hasegawa et al. |
| 6,261,809 B1 | 7/2001 | Bertling et al. |
| 6,287,768 B1 | 9/2001 | Chenchik et al. |
| 6,312,911 B1 | 11/2001 | Bancroft et al. |
| 6,326,489 B1 | 12/2001 | Church et al. |
| 6,342,359 B1 | 1/2002 | Lee et al. |
| 6,361,944 B1 | 3/2002 | Mirkin et al. |
| 6,379,897 B1 | 4/2002 | Weidenhammer et al. |
| 6,399,397 B1 | 6/2002 | Zarling et al. |

(Continued)

FOREIGN PATENT DOCUMENTS

| | | |
|---|---|---|
| DE | 2518871 A1 | 11/1975 |
| DE | 4443660 C1 | 10/1995 |

(Continued)

OTHER PUBLICATIONS

Cutler et al. Nano. Lett. 10:1477-1480. (Year: 2010).*
Billiet et al. Nature Chemistry 6:815-821. (Year: 2014).*
Kim, Jeong AH et al., "Fabrication and Characterization of a PDMS-Glass Hybrid Continuous-Flow PCR Chip", Biochemical Engineering Journal, 29, 91-97 (2006).
Curcio, Mario et al., "Continuous Segmented-Flow Poymerase Chain Reaction for High-Throughput Miniaturized DNA Amplification" Analytical Chemistry, vol. 75, No. 1, 1-7 ( Jan. 1, 2003).
Kopp, Martin U. et al, "Chemical Amplification: Continuous-Flow PCR on a Chip", Science, vol. 280, 1046-1048 (1998).

(Continued)

*Primary Examiner* — Samuel C Woolwine

(74) *Attorney, Agent, or Firm* — Clay D. Shorrock

(57) ABSTRACT

A composition comprising submicron particles covered by a monolayer of nucleic acid wherein the nucleic acid may be recovered from the submicron particles is claimed. Methods of attaching a nucleic acid to an object for authentication and methods of authenticating an object are also claimed.

14 Claims, No Drawings

(56) References Cited

U.S. PATENT DOCUMENTS

| | | |
|---|---|---|
| 6,537,747 B1 | 3/2003 | Mills, Jr. et al. |
| 6,537,752 B1 | 3/2003 | Astle |
| 6,576,422 B1 | 6/2003 | Weinstein et al. |
| 6,608,228 B1 | 8/2003 | Cumpston et al. |
| 6,613,560 B1 | 9/2003 | Tso et al. |
| 6,632,653 B1 | 10/2003 | Astle |
| 6,686,149 B1 | 2/2004 | Sanchis et al. |
| 6,703,228 B1 | 3/2004 | Landers et al. |
| 6,709,692 B2 | 3/2004 | Sudor |
| 6,743,640 B2 | 6/2004 | Whitten et al. |
| 6,995,256 B1 | 2/2006 | Li et al. |
| 7,014,113 B1 | 3/2006 | Powell et al. |
| 7,015,030 B1 | 3/2006 | Fouillet et al. |
| 7,031,927 B1 | 4/2006 | Beck et al. |
| 7,060,874 B2 | 6/2006 | Wilkins |
| 7,112,616 B2 | 9/2006 | Takizawa et al. |
| 7,115,301 B2 | 10/2006 | Sheu et al. |
| 7,133,726 B1 | 11/2006 | Atwood et al. |
| 7,160,996 B1 | 1/2007 | Cook |
| 7,223,906 B2 | 5/2007 | Davis |
| 7,250,195 B1 | 7/2007 | Storey et al. |
| 7,709,250 B2 | 5/2010 | Corbett et al. |
| 7,732,492 B2 | 6/2010 | Makino et al. |
| 8,278,807 B2 | 10/2012 | Agneray et al. |
| 8,597,549 B2 | 12/2013 | Cumpston et al. |
| 9,266,370 B2 | 2/2016 | Jung et al. |
| 9,297,032 B2 | 3/2016 | Jung et al. |
| 2001/0039018 A1 | 11/2001 | Matson et al. |
| 2002/0048822 A1 | 4/2002 | Rittenburg et al. |
| 2002/0051969 A1 | 5/2002 | Goto et al. |
| 2002/0056147 A1 | 5/2002 | Dau et al. |
| 2002/0064639 A1 | 5/2002 | Rearick et al. |
| 2002/0080994 A1 | 6/2002 | Lofgren et al. |
| 2002/0119485 A1 | 8/2002 | Morgan |
| 2002/0128234 A1 | 9/2002 | Hubbell et al. |
| 2002/0129251 A1 | 9/2002 | Itakura et al. |
| 2002/0137893 A1 | 9/2002 | Burton et al. |
| 2002/0155490 A1 | 10/2002 | Skinner et al. |
| 2002/0160360 A1 | 10/2002 | Chenchik et al. |
| 2002/0167161 A1 | 11/2002 | Butland |
| 2002/0185634 A1 | 12/2002 | Marder et al. |
| 2002/0187263 A1 | 12/2002 | Sheu et al. |
| 2003/0000225 A1 | 1/2003 | Nagai et al. |
| 2003/0017551 A1 | 1/2003 | Parthasarathy et al. |
| 2003/0031340 A1 | 2/2003 | Alattar et al. |
| 2003/0035917 A1 | 2/2003 | Hyman |
| 2003/0064507 A1 | 4/2003 | Gallagher et al. |
| 2003/0096273 A1 | 5/2003 | Gagna |
| 2003/0142704 A1 | 7/2003 | Lawandy |
| 2003/0142713 A1 | 7/2003 | Lawandy |
| 2003/0162296 A1 | 8/2003 | Lawandy |
| 2003/0173700 A1 | 9/2003 | Thomas et al. |
| 2003/0177095 A1 | 9/2003 | Zorab et al. |
| 2003/0203387 A1 | 10/2003 | Pelletier |
| 2003/0207331 A1 | 11/2003 | Wilson, Jr. et al. |
| 2004/0063117 A1 | 4/2004 | Rancien et al. |
| 2004/0071718 A1 | 4/2004 | Tsai |
| 2004/0115796 A1 | 6/2004 | Burns |
| 2004/0166520 A1 | 8/2004 | Connolly |
| 2004/0219287 A1 | 11/2004 | Regan et al. |
| 2005/0008762 A1 | 1/2005 | Sheu et al. |
| 2005/0031120 A1 | 2/2005 | Samid |
| 2005/0045063 A1 | 3/2005 | Niggemann et al. |
| 2005/0053968 A1 | 3/2005 | Bharadwaj et al. |
| 2005/0059029 A1 | 3/2005 | Mariella, Jr. et al. |
| 2005/0059059 A1 | 3/2005 | Liang |
| 2005/0089970 A1 | 4/2005 | Bradburne et al. |
| 2005/0112610 A1 | 5/2005 | Lee et al. |
| 2005/0142565 A1 | 6/2005 | Samper et al. |
| 2005/0214532 A1 | 9/2005 | Kosak et al. |
| 2005/0260609 A1 | 11/2005 | Lapidus |
| 2006/0017957 A1 | 1/2006 | Degott et al. |
| 2006/0017959 A1 | 1/2006 | Downer et al. |
| 2006/0056695 A1 | 3/2006 | Wu et al. |
| 2006/0117465 A1 | 6/2006 | Willows et al. |
| 2006/0121181 A1 | 6/2006 | Sleat et al. |
| 2006/0199196 A1 | 9/2006 | O'Banion et al. |
| 2006/0286569 A1 | 12/2006 | Bar-Or et al. |
| 2007/0012784 A1 | 1/2007 | Mercolino |
| 2007/0026239 A1 | 2/2007 | Sigrist et al. |
| 2007/0041622 A1 | 2/2007 | Salva Calcagno |
| 2007/0048761 A1 | 3/2007 | Reep et al. |
| 2007/0072197 A1 | 3/2007 | Rayms-Keller et al. |
| 2007/0117119 A1 | 5/2007 | Akita et al. |
| 2007/0121937 A1 | 5/2007 | Kochevar et al. |
| 2007/0160814 A1 | 7/2007 | Mercolino |
| 2007/0254292 A1 | 11/2007 | Fukasawa et al. |
| 2008/0038813 A1 | 2/2008 | Chen |
| 2008/0081357 A1 | 4/2008 | Kwon et al. |
| 2008/0149713 A1 | 6/2008 | Brundage |
| 2008/0153135 A1 | 6/2008 | Liu |
| 2008/0216255 A1 | 9/2008 | Poovey et al. |
| 2008/0248948 A1 | 10/2008 | Hartlep |
| 2008/0290649 A1 | 11/2008 | Klein et al. |
| 2008/0293052 A1 | 11/2008 | Liang et al. |
| 2008/0299559 A1 | 12/2008 | Kwok et al. |
| 2008/0299667 A1 | 12/2008 | Kwok et al. |
| 2008/0312427 A1 | 12/2008 | Kwok et al. |
| 2009/0042191 A1 | 2/2009 | Hayward et al. |
| 2009/0057147 A1 | 3/2009 | Kayyem |
| 2009/0069199 A1 | 3/2009 | Brandenburg |
| 2009/0075261 A1 | 3/2009 | Hayward et al. |
| 2009/0136163 A1 | 5/2009 | Kerr et al. |
| 2009/0220789 A1 | 9/2009 | DeSimone et al. |
| 2009/0222912 A1 | 9/2009 | Boschin |
| 2009/0253127 A1 | 10/2009 | Gaudreau et al. |
| 2009/0286250 A1 | 11/2009 | Hayward et al. |
| 2009/0311555 A1 | 12/2009 | Badyal et al. |
| 2009/0313740 A1 | 12/2009 | Santos et al. |
| 2009/0325234 A1 | 12/2009 | Gregg et al. |
| 2010/0050344 A1 | 3/2010 | Peltz et al. |
| 2010/0065463 A1 | 3/2010 | Taylor |
| 2010/0075407 A1 | 3/2010 | Duffy et al. |
| 2010/0075858 A1 | 3/2010 | Davis et al. |
| 2010/0099080 A1 | 4/2010 | Church et al. |
| 2010/0149531 A1 | 6/2010 | Tang |
| 2010/0240101 A1 | 9/2010 | Lieberman et al. |
| 2010/0250616 A1 | 9/2010 | Kim |
| 2010/0258743 A1 | 10/2010 | Bortolin |
| 2010/0267091 A1 | 10/2010 | Murray et al. |
| 2010/0279282 A1 | 11/2010 | Liang et al. |
| 2010/0285447 A1 | 11/2010 | Walsh et al. |
| 2010/0285490 A1 | 11/2010 | Dees et al. |
| 2010/0285985 A1 | 11/2010 | Liang et al. |
| 2010/0307120 A1 | 12/2010 | Stover |
| 2011/0014133 A1 | 1/2011 | Grunstein |
| 2011/0046205 A1 | 2/2011 | Kosak et al. |
| 2011/0054938 A1 | 3/2011 | Hood et al. |
| 2011/0165569 A1 | 7/2011 | Macula |
| 2011/0171749 A1* | 7/2011 | Alocilja ............... B82Y 30/00 436/501 |
| 2011/0229881 A1 | 9/2011 | Oshima et al. |
| 2011/0250594 A1 | 10/2011 | Liang et al. |
| 2011/0263688 A1 | 10/2011 | Barany et al. |
| 2012/0115154 A1 | 5/2012 | Hampikian |
| 2012/0264742 A1 | 10/2012 | Furuishi et al. |
| 2013/0040150 A1 | 2/2013 | Trexler et al. |
| 2013/0040381 A1 | 2/2013 | Gregg et al. |
| 2013/0046994 A1 | 2/2013 | Shaw |
| 2013/0048731 A1 | 2/2013 | Flickner et al. |
| 2013/0109596 A1 | 5/2013 | Peterson et al. |
| 2013/0149706 A1 | 6/2013 | Kwok et al. |
| 2013/0222559 A1 | 8/2013 | Lebaschi et al. |
| 2013/0234043 A1 | 9/2013 | Hussain et al. |
| 2013/0274129 A1 | 10/2013 | Katzen et al. |
| 2014/0099643 A1 | 4/2014 | Jung et al. |
| 2014/0106357 A1 | 4/2014 | Berrada et al. |
| 2014/0224673 A1 | 8/2014 | Alocilja |
| 2014/0256881 A1 | 9/2014 | Berrada et al. |
| 2014/0272097 A1 | 9/2014 | Jung et al. |
| 2014/0295423 A1 | 10/2014 | Liang et al. |
| 2015/0017444 A1 | 1/2015 | Gang et al. |
| 2015/0018538 A1 | 1/2015 | Berrada et al. |
| 2015/0030545 A1 | 1/2015 | Grass et al. |

(56) References Cited

U.S. PATENT DOCUMENTS

| | | | |
|---|---|---|---|
| 2015/0083797 A1 | 3/2015 | Tran et al. |
| 2015/0104800 A1 | 4/2015 | Lee et al. |
| 2015/0107475 A1 | 4/2015 | Jung et al. |
| 2015/0110342 A1 | 4/2015 | Suzuki |
| 2015/0125949 A1 | 5/2015 | Liss |
| 2015/0133319 A1 | 5/2015 | Fu et al. |
| 2015/0141264 A1 | 5/2015 | Jung et al. |
| 2015/0191799 A1 | 7/2015 | Liang et al. |
| 2015/0232952 A1 | 8/2015 | Sun et al. |
| 2015/0266332 A1 | 9/2015 | Szczepanik et al. |
| 2015/0275271 A1 | 10/2015 | Berrada et al. |
| 2015/0302713 A1 | 10/2015 | Berrada et al. |
| 2015/0304109 A1 | 10/2015 | Tran et al. |
| 2015/0329856 A1 | 11/2015 | Liang et al. |
| 2016/0076088 A1 | 3/2016 | Tran et al. |
| 2016/0102215 A1 | 4/2016 | Hayward et al. |
| 2016/0168781 A1 | 6/2016 | Tran et al. |
| 2016/0246892 A1 | 8/2016 | Murrah et al. |
| 2016/0264687 A1 | 9/2016 | Tran |
| 2016/0326511 A1 | 11/2016 | Berrada et al. |
| 2016/0362723 A1 | 12/2016 | Jung et al. |
| 2017/0021611 A1 | 1/2017 | Jung et al. |

FOREIGN PATENT DOCUMENTS

| | | |
|---|---|---|
| EP | 0623658 A2 | 11/1994 |
| EP | 0477220 B1 | 9/1996 |
| EP | 0840350 A2 | 5/1998 |
| EP | 1063286 A1 | 12/2000 |
| EP | 1231470 A1 | 8/2002 |
| EP | 1237327 A2 | 9/2002 |
| EP | 1403333 A1 | 3/2004 |
| EP | 1847316 A1 | 10/2007 |
| EP | 2428925 A1 | 3/2012 |
| EP | 2444136 A1 | 4/2012 |
| EP | 2444546 A1 | 4/2012 |
| GB | 2319337 A | 5/1998 |
| GB | 2434570 A | 8/2007 |
| JP | 63-503242 | 11/1988 |
| JP | 2009517250 A | 4/2009 |
| JP | 2011036278 A | 2/2011 |
| JP | 2013235553 A | 11/2013 |
| RU | 2084535 C1 | 7/1997 |
| RU | 2170084 C1 | 7/2001 |
| WO | WO87/06383 A1 | 10/1987 |
| WO | WO90/14441 A1 | 11/1990 |
| WO | WO92/04469 A2 | 3/1992 |
| WO | WO95/02702 A1 | 1/1995 |
| WO | WO95/06249 A1 | 3/1995 |
| WO | WO97/04392 A1 | 2/1997 |
| WO | WO97/45539 A1 | 12/1997 |
| WO | WO98/06084 A1 | 2/1998 |
| WO | WO98/16313 A1 | 4/1998 |
| WO | WO99/45514 A1 | 9/1999 |
| WO | WO99/59011 A1 | 11/1999 |
| WO | WO00/55609 A2 | 9/2000 |
| WO | WO00/61799 A2 | 10/2000 |
| WO | WO01/25002 A1 | 4/2001 |
| WO | WO01/36676 A2 | 5/2001 |
| WO | WO01/99063 A1 | 12/2001 |
| WO | WO02/057548 A1 | 7/2002 |
| WO | WO02/066678 A2 | 8/2002 |
| WO | WO02/084617 A1 | 10/2002 |
| WO | WO03/016558 A1 | 2/2003 |
| WO | WO03/030129 A2 | 4/2003 |
| WO | WO03030129 A2 | 4/2003 |
| WO | WO03/038000 A1 | 5/2003 |
| WO | WO03/080931 A1 | 10/2003 |
| WO | WO2004/025562 A1 | 3/2004 |
| WO | WO2004/086323 A1 | 10/2004 |
| WO | WO2004087430 A1 | 10/2004 |
| WO | WO2005/075683 A1 | 8/2005 |
| WO | WO2005/103226 A2 | 11/2005 |
| WO | WO2005108103 A2 | 11/2005 |
| WO | WO2006/109014 A1 | 10/2006 |
| WO | WO2007037586 A1 | 4/2007 |
| WO | WO2007/078833 A2 | 7/2007 |
| WO | WO2008/007060 A1 | 1/2008 |
| WO | WO2008045288 A2 | 4/2008 |
| WO | WO2008/154931 A1 | 12/2008 |
| WO | WO2009/027806 A1 | 3/2009 |
| WO | 2011/005222 A1 | 1/2011 |
| WO | WO 2011/005222 A1 | 1/2011 |
| WO | WO2012/076021 A1 | 6/2012 |
| WO | WO2013/052924 A1 | 4/2013 |
| WO | WO2013/154943 A1 | 10/2013 |
| WO | WO2013/170009 A1 | 11/2013 |
| WO | WO2014/062754 A1 | 4/2014 |
| WO | WO 2014006726 A1 | 6/2016 |

OTHER PUBLICATIONS

Skirtach, Andre, G. et al, "The Role of Metal Nanoparticles in Remote Release of Encapsulated Materials", Nano Letters, vol. 5, No. 7, 1371-1377 (2005).
Fixe, F. et al., Thin Film Micro Arrays with Immobilized DNA for Hybridization Analysis, Mat. Res. Soc. Symp. Proc. vol. 723, Materials Research Society, O23.1-O23.6 (2002).
Hayward, Jim et al., "A Scaled, Integrative Implementation for DNA Marking of Integrated Circuits", Applied DNA Sciences, 1-25 (2013).
Ovsianikov, Aleksandr et al., "Two-Photon Polymerization Technique for Microfabrication of CAD-Designed 3D Scaffolds from Commercially Available Photosensitive Materials", Journal of Tissue Engineering and Regenerative Medicine, 1:443-449 (2007).
Khandjian, E.W., "Optimized Hybridization of DNA Blotted and Fixed to Nitrocellulose and Nylon Membranes" Biotechnology, vol. 5, 165-167 (1987).
Chrisey, Linda A et al., "Fabrication of Patterned DNA Surfaces", Nucleic Acids Research, vol. 24, No. 15, 3040-3047 (1996).
Wollenberger, Louis V. et al.,"Detection of DNA Using Upconverting Phosphor Reporter Probes", SPIE, vol. 2985, 100-111 (1997).
Takara Bio, "Takara Bio to Produce DNA Fragments for DNA Microarrays on Industrial Scale", http://www.evaluategroup.com/Universal/View.aspx?type_Story&id.
Obeid, Pierre J. et al., "Microfabricated Device for DNA and RNA Amplification by Continuous-Flow Polymerase Chain Reaction and Reverse Transcription-Polymerase Chain Reaction with Cycle Number Section", Anal. Chem, 75, 288-295 (2003).
Supplemental European Search Report for Corresponding European Patent Application No. EP14820538.8, pp. 1-8 (dated Jan. 25, 2017).
Hashimoto, Masahiko et al., "Rapid PCR in a Continuous Flow Device", Lab Chip, 4, 638-645 (2004).
Thibaudau, Franck, "Ultrafast Photothermal Release of DNA from Gold Nanoparticles", J. Phys. Chem. Lett. 3, 902-907 (2012).
Berger, S.A. et al., "Flow in Curved Pipes", Ann. Rev. Fluid Mech., 15:461-512 (1983).
Written Opinion of the International Search Authority for PCT/US2015/013084 dated Apr. 17, 2015.
Ageno, M., et al., "The Alkaline Denaturation of DNA", Biophys J., Nov. 1969; 9(11): 1281-1311.
Hou, Sen, et al., "Method to Improve DNA Condensation Efficiency by Alkali Treatment", Taylor & Francis, Nucleosides, Nucleotides and Nucleic Acids, 28:725-735, 2009.
Thiel, Teresa, et al., "New zwitterionic butanesulfonic acids that extend the alkaline range of four families of good buffers: Evaluation for use in biological systems", J. Biochem. Biophys., Methods 37 (1998) 117-129.
Schulz, M.M., et al., "Archived or directly swabbed latent fingerprints as a DNA source for STR typing", Forensic Science International 127 (2002) 128-130.
Park, H., et al., "Stress response of fibroblasts adherent to the surface of plasma-treated poly(lactic-co-glycolic acid) nanofiber matrices", Colloids Surf B Biointerfaces, May 1, 2010, 1;77(1); 90-5.
WiseGeek, "How Many Species of Bacteria Are There", http://www.wisegeek.org/how-many-species-of-bacteria-are-there.htm.

(56) References Cited

OTHER PUBLICATIONS

Wikipedia, "List of sequenced bacterial genomes", http://en.wikipedia.org/wiki/List_of_sequenced_bacterial_genomes.
Wikipedia, "Virus", http://en.wikipedia.org/wiki/Virus.
Agrawal, Sudhir, et al., "Site-Specific Functionalization of Oligodeoxynucleotides for Non-Radioactive Labelling", Tetrahedron Letters, vol. 31, No. 11, pp. 1543-1546, 1990.
Beija, Mariana, et al., "Synthesis and applications of Rhodamine derivatives as fluorescent probes", Chem. Soc. Rev., 2009, 38, 2410-2433.
Corstjens, P.L.A.M., et al., "Infrared up-converting phosphors for bioassays", IEE Proc.-Nanobiotechnol., vol. 152, No. 2, Apr. 2005.
Tyagi, Sanjay, et al., "Multicolor molecular beacons for allele discrimination", Nature Biotechnology, vol. 16, Jan. 1996.
Gibson, U.E., et al., "A novel method for real time quantitative RT-PCR", Genome Res., 1996, 6:995-1001.
Gupta, K.C., et al., "A general method for the synthesis of 3'-sulfhydryl and phosphate group containing oligonucleotides", Nucleic Acids Research, vol. 19, No. 11, p. 3019-3025 (1991).
Heid, C.A., et al., "Real time quantitative PCR", Genome Res. 1996 6:986-994.
Holland, Pamela, M., et al., "Detection of specific polymerase chain reaction product by utilizing the 5' → 3' exonuclease activity of Thermus aquaticus DNA polymerase", Proc. Natl. Acad. Sci. USA, vol. 88, pp. 7276-7280, Aug. 1991, Biochemistry.
Hosokawa, Kazuo, et al., "DNA Detection on a Power-free Microchip with Laminar Flow-assisted Dendritic Amplification", Analytical Sciences, Oct. 2010, vol. 26.
Hussein, Ebtissam, H.A., et al., "Molecular Characterization of Cotton Genotypes Using PCR-based Markers", Journal of Applied Sciences Research, 3(10): 1156-1169, 2007.
Ibrahim, Rashid Ismael Hag, et al., "Complete Nucleotide Sequence of the Cotton (*Gossypium barbadense* L.) Chloroplast Genome with a Comparative Analysis of Sequences among 9 Dicot Plants", Genes Genet. Syst. (2006) 81, p. 311-321.
Jiang, Chun-Xiao, et al., "Polyploid formation created unique avenues for response to selection in *Gossypium* (cotton)", Proc. Natl. Acad. Sci. USA, vol. 95, pp. 4419-4424, Apr. 1998.
Kaneda, Shohei, et al., "Modification of the Glass Surface Property in PDMS-Glass Hybrid Microfluidic Devices", Analytical Sciences, Jan. 2012, vol. 28.
Karahan, H.A., et al., "Improvements of Surface Functionality of Cotton Fibers by Atmospheric Plasma Treatment", Fibers and Polymers 2008, vol. 9, No. 1, 21-26.
Lee, Seung-Bum, et al., "The complete chloroplast genome sequence of Gossypium hirsutum: organization and phylogenetic relationships to other angiosperms", BMC Genomics 2006, 7:61.
Lee, Linda G., et al., "Allelic discrimination by nick-translation PCR with fluorogenic probes", Nucleic Acids Research, 1993, vol. 21, No. 16, 3761-3766.

Tyagi, Sanjay, et al., "Molecular Beacons: Probes that Fluoresce upon Hybridization", Nature Biotechnology, vol. 18, Mar. 1996.
Sproat, Brian S. et al., "The synthesis of protected 5'-mercapto-2',5'-dideoxyribonucleoside-3'-O-phosphoramidites; uses of 5'-mercapto-oligodeoxyribonucleotides", Nucleic Acids Research, vol. 15, No. 12, 1987.
Nazarenko, I.A., et al., "A closed tube format for amplification and detection of DNA based on energy transfer", Nucleic Acids Research, 1997, vol. 25, No. 12, 2516-2521.
Nelson, Paul S., et al., "Bifunctional oligonucleotide probes synthesized using a novel CPG support are able to detect single base pair mutations", Nucleic Acids Research, vol. 17, No. 18, 1989.
Yang, XF, et al., "Fluorimetric determination of hemoglobin using spiro form rhodamine B hydrazide in a micellar medium", Talanta Nov. 12, 2003; 61(4): 439-45.
Written Opinion of the International Searching Authority issued in PCT/US15/21165 dated Jul. 2, 2015.
Tuzlakoglu, K., et al., "A new route to produce starch-based fiber mesh scaffolds by wet spinning and subsequent surface modification as a way to improve cell attachment and proliferation", Journal of Biomedical Materials Research Part A, 2009, Wiley Periodicals, Inc, p. 369-377.
Zuckermann, Ronald, et al., "Efficient methods for attachment of thiol specific probes to the 3'-ends of synthetic oligodeoxyribonucleotides", Nucleic Acids Research, vol. 15, No. 13, 1987.
Annex 5, WHO good Distribution Practices for Pharmaceutical Products, WHO Technical Report Series, No. 957, pp. 235-264 (2010).
Notice of Reasons for Rejection issued in Japanese Patent Application No. JP2016-562831 dated Jul. 3, 2017.
Supplementary European Search Report for corresponding European Application No. EP15765671, p. 1-7, Oct. 30, 2017.
Extended European Search Report issued in European Patent Application No. 14852842.5 dated Jun. 12, 2017.
International Preliminary Report on Patentability issued in PCT/US2013/065161 dated Apr. 21, 2015.
Ullrich, Thomas, et al., "Competitive Reporter Monitored Amplification (CMA)—Quantification of Molecular Targets by Real Time Monitoring of Competitive Reporter Hybridization", Plos One, Apr. 2012, vol. 7, Issue 4.
Van De Rijke, Frans, et al., "Up-converting phosphor reporters for nucleic acid microarrays", Nature Publishing Group, Nature Biotechnology 19, Mar. 2001, 273-276.
Whitcombe, David, et al., "Detection of PCR products using self-probing amplicons and fluorescence", Nature Biotechnology, vol. 17, Aug. 1999, p. 804-807.
Hunicke-Smith, Scott P., "PCR and Cycle Sequencing Reactions: A New Device and Engineering Model", Dissertation, Stanford University, pp. i-xiv and 1-200, May 1997.

* cited by examiner

NUCLEIC ACID COATED SUBMICRON PARTICLES FOR AUTHENTICATION

CROSS-REFERENCE TO RELATED APPLICATION

This application claims the benefit of U.S. Provisional Application No. 62/461,312, filed on Feb. 21, 2017, which is hereby incorporated by reference in its entirety.

BACKGROUND OF THE INVENTION

Nucleic acids have been permanently conjugated to metal oxides for use as biosensors and for biomedical diagnosis, therapy, and catalysis. Additionally, DNA has been used as a taggant for purposes of authenticating objects. For example, in U.S. Pat. No. 9,297,032, DNA is mixed with a perturbant and a polymer to coat an object. The DNA may be recovered from the object and PCR-based assays are performed to verify the taggant, thus authenticating the object.

However, there remains a need to incorporate nucleic acid taggants into materials that cannot be introduced into water, i.e., are water immiscible, materials which are not or cannot be produced using water, or materials in which the raw materials are often comprised of powders, e.g., pharmaceuticals and cosmetics. In addition there remains a further unmet need for a method of removably attaching a nucleic acid taggant to a submicron particle, such that the nucleic acid can be later readily removed from the submicron particle for the purpose of authentication.

SUMMARY OF THE INVENTION

The present inventors have found a means of removably affixing a monolayer of nucleic acid onto the surface of submicron particles so that the nucleic acid may be later readily recovered and isolated from the submicron particle.

In one embodiment, the invention relates to a composition including submicron particles covered by a monolayer of nucleic acid, wherein the nucleic acid may be recovered from the submicron particles. The nucleic acid is preferably affixed to the submicron particles.

The preferred nucleic acid is deoxyribonucleic acid (DNA). The preferred submicron particles are metal oxides. Preferred metal oxides are titanium dioxide and silicon dioxide.

The submicron particles may be exposed to a substance to optimize the desired level of adhesion of nucleic acid to submicron particles so the nucleic acid may be recovered from the submicron particles. Preferably, the substance is selected from the group consisting of sodium phosphate, borate, monopotassium phosphate, vanadate, citrate, ethylenediaminetetraacetic acid, sodium dodecyl sulfate, and sodium lauryl sulfate.

In another embodiment, the invention relates to a method of attaching a nucleic acid to an object for authentication purposes comprising providing a plurality of submicron particles; adding an amount of nucleic acid suspended in a solvent to the submicron particles so that only enough nucleic acid is present to form a monolayer around each submicron particle; extracting the solvent to form a monolayer of nucleic acid covering each submicron particle; and attaching the nucleic acid covered submicron particles to an object to be authenticated using nucleic acid amplification and/or taggant sequence detection techniques for authentication. Preferably the solvent is water.

In another embodiment, the invention relates to a method of authenticating an object comprising providing a plurality of submicron particles; adding an amount of nucleic acid suspended in a solvent to the submicron particles so that only enough nucleic acid is present to form a monolayer around each submicron particle; extracting the solvent to form a monolayer of nucleic acid covering each submicron particle; attaching the nucleic acid covered submicron particles to an object to be authenticated; taking a sample of the object to recover the nucleic acid from the submicron particles; isolating the nucleic acid; amplifying and identifying the nucleic acid using nucleic acid amplification and/or taggant sequence detection techniques; and verifying the authenticity of the object by the presence of the nucleic acid.

DETAILED DESCRIPTION

A composition including submicron particles covered by a removably affixed monolayer of nucleic acid taggants is claimed. The nucleic acid taggant may be readily or otherwise removed from the submicron particles so the nucleic acid taggant may be amplified and identified using nucleic acid amplification and/or taggant sequence detection techniques.

Submicron particles measure under 1 μm (1,000 nm) in diameter. The submicron particles of the invention include any submicron particle that can be incorporated within an object or attached to an object. Preferred submicron particles are spherical, have known circumferences, disburse well in water, and provide advantageous binding conditions for a nucleic acid.

Examples of submicron particles include metal oxides, metal carbides, metal nitrides, and metal sulfates. The preferred submicron particles are metal oxides. Preferred metal oxides such as silicon dioxide, titanium dioxide, and aluminum dioxide may be incorporated into pharmaceuticals, foods, and cosmetics as excipients or active ingredients. In addition, the metal oxide submicron particles can be incorporated into most commercially available materials including, for example, thermoplastics, acrylics, textiles, and polymers, without causing adverse structural effects.

The nucleic acid is used as a taggant, i.e., a substance that is affixed to an object to provide information about the object such as the source of manufacture, national origin, or authenticity. "Nucleic acid" and "nucleic acid taggant" are used interchangeably throughout the application. Nucleic acid includes DNA and ribonucleic acid (RNA). Preferably, the nucleic acid taggant is a non-naturally occurring sequence that is adapted for use in authentication. The preferred nucleic acid is DNA.

Nucleic acid taggants useful in the invention include any suitable nucleic acid taggant, including DNA taggants. In one example, the DNA taggant is a double stranded DNA molecule having a length of between about 20 base pairs and about 1000 base pairs. In another example, the DNA taggant is a double-stranded DNA molecule with a length of between about 80 and 500 base pairs. In another example, the DNA taggant is a double-stranded DNA molecule having a length of between about 100 and about 250 base pairs. Alternatively, the DNA taggant can be single-stranded DNA of any suitable length, such as between about 20 bases and about 1000 bases; between about 80 bases and 500 bases; or between about 100 bases and about 250 bases. The DNA taggant can be a naturally-occurring DNA sequence, whether isolated from natural sources or synthetic; or the DNA taggant can be a non-naturally occurring sequence produced from natural or synthetic sources. All or a portion of the DNA may comprise an identifiable sequence. The preferred DNA is double-stranded DNA of a non-naturally occurring sequence.

Preferably, the DNA taggant is identifiable by any suitable nucleic acid amplification and/or taggant sequence detection technique. Nucleic acid amplification may be accomplished via any technique known in the art, such as, for example, polymerase chain reaction (PCR), loop mediated isothermal amplification, rolling circle amplification, nucleic acid sequence base amplification, ligase chain reaction, or recombinase polymerase amplification. In addition, any known sequence detection and/or identification technique may be used to detect the presence of the nucleic acid taggant such as, for example, hybridization with a taggant-sequence specific nucleic acid probe, an in situ hybridization method (including fluorescence in situ hybridization: FISH), as well as amplification and detection via PCR, such as quantitative (qPCR)/real time PCR (RT-PCR). Isothermal amplification and taggant sequence detection may also be performed with the aid of an in-field detection device such as the T-16 Isothermal Device manufactured by TwistDX, Limited (Hertfordshire, United Kingdom).

In order to identify the nucleic acids, and thus authenticate an associated object, it is important that the nucleic acids be readily removable from the object to which they are applied. In other words, enough nucleic acid must be removable from the object to enable nucleic acid amplification and/or taggant sequence detection techniques. Removal of nucleic acids from an object may be performed via the removal of nucleic acids from the surface of the object without the removal of the nucleic acids' associated submicron particle. Removal of nucleic acids may also be accomplished via the removal of one or more nucleic acid-coated submicron particles attached to an object. The nucleic acid is then disassociated from the recovered submicron particle(s), as described herein, so that the nucleic acids can be amplified and identified using nucleic acid amplification and/or taggant sequence detection techniques.

"Readily removing the nucleic acid from the object to which it was applied" is defined as removing the nucleic acid and/or DNA-coated submicron particles in a manner that is not laborious. For example, "readily removing the nucleic acid from the object to which it was applied" includes wiping the surface of the object the nucleic acid-covered submicron particles are attached to with a wet cotton swab. In another example, "readily removing the nucleic acid from the object to which it was applied" includes using a cotton swab with methyl ethyl ketone to wipe the object. In an additional example, "readily removing the nucleic acid from the object to which it was applied" includes using a competitive binding substance to detach the nucleic acids- or DNA-coated submicron particles from the object.

In order to allow the nucleic acid to be readily removed from the submicron particles, the submicron particles may be treated with a competitive binding substance to optimize the desired level of adhesion of nucleic acid to the submicron particles before the nucleic acid is affixed to the submicron particles. The submicron particles may be treated with the competitive binding substance before or after the nucleic acid is affixed to the submicron particles. Optimal adhesion would allow for the nucleic acid taggant to adhere to the submicron particles so that the taggant remains affixed throughout the submicron particles' lifecycle, but the adhesion cannot be so strong that not enough nucleic acid taggant can be removed from the submicron particles to allow for the use of nucleic acid amplification and/or taggant sequence detection techniques when authentication is later desired.

For example, titanium dioxide is known to bond strongly to a nucleic acid. As a result, it is difficult to remove the nucleic acid affixed to an untreated titanium dioxide submicron particle when authentication is desired. In addition, due to the high level of adhesion between nucleic acid and untreated titanium dioxide, the nucleic acid can be damaged during the removal process. To address this problem, a titanium dioxide submicron particle may be treated with a competitive binding substance to reduce the submicron particle's bonding strength vis a vis nucleic acid such that when the titanium dioxide submicron particles are exposed to the nucleic acid taggant, the bonding forces between the nucleic acid and the titanium dioxide submicron particles will be permanently weakened, thus allowing for the ready removal of the nucleic acids when authentication is desired.

Nucleic acids bind to metal oxide submicron particles via the non-covalent bonding of the nucleic acid's phosphate backbone to the metal oxides' surface hydroxyl groups. An advantageous competitive binding substance to pre-treat the metal oxide submicron particles to aid in nucleic acid recovery for authentication may be any substance that will competitively bond to the surface hydroxyl groups of the metal oxide submicron particles, thus reducing overall non-covalent bonding strength between the nucleic acid and the metal oxide submicron particle. Preferred competitive binding substances include sodium phosphate, borate, vanadate, citrate, ethylenediaminetetraacetic acid, monopotassium phosphate, sodium dodecyl sulfate, and sodium lauryl sulfate. The competitive binding substances may be used before or after a submicron particle is introduced to nucleic acids. A submicron particle may also be treated with a competitive binding substance after the formation of the nucleic acid monolayer to facilitate the removal of the nucleic acid from the submicron particle, and to also inhibit the nucleic acid from rebinding to a submicron particle at the time of authentication.

A substance may also be used to pre-treat submicron particles that do not bond well to nucleic acids, or if the binding strength of nucleic acids needs to be increased. In one embodiment titanium dioxide submicron particles may be treated with hydrochloric acid or other acids to increase binding strength by protonating oxygen.

The method of covering submicron particles with a monolayer of nucleic acid involves providing a plurality of uniform submicron particles. The submicron particles may be treated with a competitive binding substance to optimize the desired level of adhesion of nucleic acid to submicron particles as discussed above. Alternatively, the submicron particles may be treated with an acid such as hydrochloric acid to increase nucleic acid binding strength. Then, nucleic acid suspended in a solvent, preferably water at a pH<4, is added to the submicron particles. The nucleic acid solution and submicron particles may be combined by methods known in the art such as stirring, vortexing, agitating, or centrifuging. Adding the correct amount of nucleic acid molecules to the solution is important for creating a monolayer of nucleic acid around each submicron particle. The correct amount of nucleic acid molecules in the solution is the exact amount of nucleic acid molecules necessary to form a monolayer of nucleic acid around each submicron particle, based upon the calculated surface area of the submicron particles and the nucleic acid molecules. These surface areas may be calculated by the methods described below. The competitive binding substance may also be applied after the nucleic acid is introduced to the submicron particles.

The total surface area of a known mass of spherical submicron particles may be calculated by using the size, i.e., diameter of the submicron particles. The surface area of a sphere is $4\pi r^2$, where r is the radius of the submicron particle, i.e., half of the diameter. If the mass of an individual submicron particle is known, the total number of submicron particles in the total mass can then be calculated. Therefore, the total surface area of a mass of uniform spherical submicron particles can be calculated.

Likewise, the surface area of a nucleic acid molecule can be calculated based upon the number of base pair in a specific sequence. In regards to B-DNA (the most common form of DNA), a base pair is 3.4 Å in length. The approximate width of double stranded B-DNA is 20 Å. The length and width of all other forms of nucleic acids are also known. Therefore, the number of nucleic acid molecules necessary to create a monolayer around each submicron particle can be calculated by dividing the surface area of the submicron particle by the surface area of the nucleic acid sequence. This number of nucleic acids can then be multiplied by the number of submicron particles in a given mass. The calculated number of nucleic acid molecules can then be converted into a mass quantity via known methods of calculation or by directly measuring with known devices.

The precise number of nucleic acid molecules in a solution can be accurately measured using known methods and devices. Devices such as the Bioanalyzer (Agilent Technologies, United States), the Qubit (ThermoFisher Scientific, United States) and/or the Nanodrop (Thermo Scientific, United States) can precisely measure nucleic acid concentrations in a solution, and thus, the number of nucleic acid molecules in a solution. In addition, qPCR can be used to determine the absolute quantification of the number of nucleic acid molecules in a solution through known methods.

The duration and extent of combining the nucleic acid solution with the submicron particles may be determined by a person having ordinary skill in the art so that the nucleic acid may form a monolayer about each submicron particle.

After a monolayer of nucleic acid is formed about each submicron particle, the solvent may be removed by known techniques such as vacuum, centrifuge, heating, evaporation, use of a desiccant, and the like. The resulting product is a monolayer of nucleic acid covering each submicron particle.

The nucleic acid covered submicron particles may then be attached to an object. The relative quantity of nucleic acid submicron particles attached to an object may vary based upon the target object's material, manufacturing process, storage conditions, use conditions, exposure to ultra violate light, or other variables that may affect the integrity of nucleic acids. Any means of attaching the nucleic acid covered submicron particles to an object may be employed, including any known method of attaching submicron particles to an object. For example, the nucleic acid covered submicron particles may be included in a pharmaceutical composition as an excipient. In another example, the nucleic acid covered submicron particles may be included in a cosmetic composition as an active ingredient. The nucleic acid covered submicron particles may also be included into the master batch of thermoplastic or acrylic based materials such that the final product contains the submicron particles. Furthermore, the nucleic acid covered submicron particles may be included into any water immiscible solutions and/or water prohibitive materials such as cyanoacrylates, polyurethane, lacquers, shellacs, epoxy based-compounds, and acrylic compounds. Alternatively, the nucleic acid covered submicron particles may be attached to the outside of an object or incorporated into the material that comprises the object.

The object may then be authenticated at a later time. Authentication of the object may involve removing a quantity of nucleic acid from the submicron particles attached to the object. As mentioned above, it is preferable that the nucleic acid is readily removed from the submicron particles and the object. Methods of removing the nucleic acid from the submicron particles are known. Some methods of removing the nucleic acid are discussed above. In one embodiment, the material of the object may be dissolved by a solvent in order to remove one or more submicron particles from the object. The nucleic acid on the recovered submicron particles may then be removed from the particle(s) and isolated. In one embodiment, the nucleic acid is removed from the submicron particles by using a solution containing a high concentration of a competitive binding substance. The high concentration of competitive binding substance causes the nucleic acids to release from the submicron particles and inhibits the nucleic acids from rebinding to the particles, thus allowing the nucleic acids to stay in solution. The solution is then utilized for identifying the nucleic acid via nucleic acid amplification and/or taggant sequence detection techniques.

Once the nucleic acid is removed from the submicron particles and isolated, nucleic acid amplification and/or taggant sequence detection techniques may be employed to amplify and identify the nucleic acid taggant. For example, in a PCR-based identification method, the nucleic acid, e.g., DNA taggants recovered from the object are isolated and then amplified by polymerase chain reaction (PCR) and resolved by gel electrophoresis, capillary electrophoresis, or the like. Since the nucleic acid sequence of the nucleic acid taggants of the present invention are unique and specific to the tagged object, the nucleic acid taggant will be amplified during PCR only by use of primers having specific sequences complementary to a portion of the unique taggant sequence. Through this procedure, if the examined object carries the nucleic acid taggant, the PCR procedure will amplify the extracted nucleic acid to produce known and detectable amplicons of a predetermined size and a sequence. In contrast, if the sample recovered from the examined object does not include the unique nucleic acid sequence corresponding to the taggant of the authentic object, there will likely be no amplified nucleic acid product, or if the primers do amplify the recovered nucleic acid to produce one or more random amplicons, these one or more amplicons cannot have the unique taggant nucleic acid sequence from the authentic object. Furthermore, the random amplicons derived from counterfeit articles are also of random lengths and the likelihood of producing amplicons of the exact lengths specified by the taggant-specific primers is very small. Therefore, by comparing the length and quantity of PCR amplicons, the authenticity of labeled objects can be verified, non-authentic objects can be screened and rejected, and anti-counterfeit screening purposes are then achieved. The DNA may also be amplified by any known isothermal amplification technique.

The quantity of amplicons and the lengths of the amplicons can be determined after any molecular weight or physical dimension-based separation, such as for instance and without limitation, gel electrophoresis in any suitable matrix medium for example in agarose gels, polyacrylamide gels or mixed agarose-polyacrylamide gels, or the electrophoretic separation can be in a slab gel or by capillary electrophoresis. RT-PCR and/or qPCR may also be used to detect the presence of the nucleic acid taggant via interrogation of amplicon quantity and length during amplification. In addition, the nucleic acid taggant may be identified by amplification in conjunction with any suitable specific marker sequence detection methods.

Examples have been set forth below for the purpose of illustration and to describe the best mode of the invention at the present time. The scope of the invention is not to be in any way limited by the examples set forth herein.

EXAMPLES

Example 1

DNA Monolayer Calculation for a 300 nm Spherical Titanium Dioxide Particle

The number of nucleic acid molecules needed to cover a mass of 300 nm diameter titanium dioxide particles was calculated. In this example, the nucleic acid was double-stranded DNA comprised of a known 400 base pair sequence.

The surface area of a single 300 nm diameter titanium dioxide particle is calculated by the formula $SA=4\pi r^2$, where SA equals the surface area of a sphere and r is the sphere's radius. Applied to the subject 300 nm diameter titanium dioxide particle, the following calculation can be made: $4 \times 3.14 \times (300 \text{ nm}/2)^2$. This calculation reveals that each individual 300 nm diameter titanium dioxide particle has a surface area of 2,826,000 Å. The total surface area of any mass 300 nm diameter titanium dioxide particle can be calculated based upon the known weight of each particle.

Since DNA is a rod-like shape, the area of a DNA molecule can be calculated by multiplying its length by its width. Here, the subject DNA molecule is 400 base pairs in length. It is known that each base pair is equal to 3.4 Å. Thus, the subject DNA molecule has a length of 1,360 Å. It is also known that double stranded DNA is 20 Å in width. Based upon these figures, the subject 400 base pair double stranded DNA molecule has a surface area of 27,200 Å.

Therefore, the number of DNA molecules necessary to create a monolayer around a single 300 nm diameter titanium dioxide particle is equal to 2,826,000 Å/27,200 Å, which is equal to 103.90 DNA molecules. With this value known, a solution containing the precise number of DNA molecules to form a monolayer around any mass of 300 nm diameter titanium dioxide submicron particles can be calculated using the methods outlined above.

Example 2

Attaching and Releasing a DNA Monolayer to 300 nm Diameter Titanium Dioxide Particles with HCl Pretreatment A stock suspension containing 20 mg of 300 nm titanium dioxide particles per mL suspended in 10 mM hydrochloric acid and water solution at pH 2 was prepared. From this stock suspension, a 500 µL amount was removed. The number of DNA molecules necessary to create a monolayer around the titanium dioxide submicron particles contained in the 500 µL suspension was calculated as described above.

The number of DNA molecules necessary to form a monolayer around every 300 nm titanium dioxide particle contained in the 500 µL suspension was calculated and added. The combined titanium dioxide particle suspension and DNA was then vortexed for 20 seconds and then centrifuged at 10 k for one minute. The resultant supernatant was removed. The remaining solid residue comprised the titanium dioxide submicron particles contained in the 500 µL suspension coated with a monolayer of DNA. The DNA coated titanium dioxide submicron particles were allowed to completely dry. Due to the pre-treatment of the 300 nm titanium dioxide particles with hydrochloric acid at a low pH, the DNA is extremely tightly bound to the titanium dioxide particles.

For DNA extraction, the DNA-coated titanium dioxide particles were re-suspended in 10 µL of 100 mM $KH_2PO_4$ (monopotassium phosphate) at a pH of approximately 9.5. The sample was vortexed and heated at 95° C. for three minutes. The sample was then centrifuged at 10 k for one minute. The resultant supernatant was removed and used for PCR-based analyses. After the PCR run, the PCR products were analyzed via capillary electrophoreses. DNA was successfully recovered from four different samples of DNA-coated titanium dioxide particles.

Example 3

Attaching DNA Taggant to Food-Grade $TiO_2$ and Incorporating it into a Dry Powder Film Coating System Food-grade $TiO_2$ powder was provided. The $TiO_2$ was pre-treated with a competitive binding substance, i.e., a phosphate in a weak acid. The amount of DNA taggant needed to cover the $TiO_2$ particles was calculated as in Example 1. The DNA was combined with the pre-treated $TiO_2$ as in Example 2. The resultant DNA-$TiO_2$ complex was mixed with untagged $TiO_2$ and then incorporated into a dry powder film coating system containing polymer, plasticizer, and pigment.

A series of DNA-tagged powder film coating and un-tagged powder film coating were prepared and sent to the laboratory for blind testing.

Protocol: The samples were labeled as samples #34, #36, #40, #41, #47, #49, #51, #57, #62, #63, #65, #66 and Placebo. Five different aliquots of each sample were taken and prepared for analysis at the laboratory. For each sample preparation, 50 mg of powder was weighed into a 1.5 ml Eppendorf tube and 5000 of DNA desorption solution (monopotassium phosphate at a pH of approximately 9.5) was added to each tube. The samples were vortexed for approximately 30 seconds, incubated at room temperature for 45 minutes, heated to 95° C. for 3 minutes and then centrifuged at 17,000 g for 5 minutes. The supernatant of each preparation was then tested using the lab-scale Step One Plus™ Real-Time PCR System (qPCR).

Results: Ct (threshold cycle) values were obtained for all reactions and the average of the five sample preparations was calculated for each sample. Based on the well-known log base two relationship between Ct and input DNA concentration, one-Ct decrease in the qPCR data corresponds to a two-fold increase in input DNA. Ct values in the 35 range are near to the detection limit relative to background. Thus, placebo controls should display Ct values of approximately 35.

Thus, the data suggest that the DNA-free placebo, plus samples #36, #49, #63 and #65 do not display significant DNA in the present assay. At the other extreme, samples #34, #40, #41, #47, #51, #57, #62 and #66 (with Ct values near to 25) display a difference in Ct between 5-9 units, indicative of a 100-fold to 1000-fold higher-input DNA concentration.

Conclusion: Samples #36, #49, #63, #65 and Placebo are indistinguishable from each other and as a set, are generally indistinguishable from background. Samples #34, #40, #41, #47, #51, #57, #62 and #66 are readily distinguishable from background and appear to contain higher amounts of DNA, with samples #62 and #66 having the highest apparent DNA concentration, reflective of 10× more DNA (3-4 fold lower Ct) than samples #34, #40 and #41 and approximately 2× more DNA (1 fold lower Ct) than samples #47, #51 and #57.

DNA was detected in the appropriate samples via qPCR and no DNA was detected in the untagged samples.

Example 4

Attaching DNA Taggant to Food-Grade $TiO_2$ and Incorporating it into a Dry Powder Film Coating System Applied to Tablet Dosage Form The tagged powder film coating formulations made according Example 3 were used to coat tablet dosage forms. Control samples were also prepared in which un-tagged powder film coatings were used to coat tablets. The resulting samples of tablets and tagged powder film coating were sent to the laboratory for blind testing.

A) Testing of Tagged Powder Film Coating Formulations

Protocol: Powder film coating samples were labeled as sample #68, #69 and #70. Five different aliquots of each sample were taken and prepared for analysis at the laboratory. For each sample preparation, 50 mg of powder was weighed into a 1.5 ml Eppendorf tube and 5000 of DNA desorption solution (monopotassium phosphate at a pH of approximately 9.5) was added to each tube. The samples were vortexed for approximately 30 seconds, incubated at room temperature for 45 minutes, heated to 95° C. for 3 minutes then centrifuged at 17,000 g for 5 minutes. The supernatant of each preparation was then tested using the lab-scale StepOnePlus™ Real-Time PCR System (qPCR).

Results: Ct (threshold cycle) values were obtained for all reactions and the average of the five sample preparations was calculated for each sample. Average Ct values for each sample were obtained. Based on the well-known log base two relationship between Ct and input DNA concentration, a one-Ct decrease in the qPCR data corresponds to a two-fold increase in input DNA. Ct values in the 35 range are near to the detection limit relative to background, thus Ct values around 35 and above can be considered to contain no measurable DNA.

Conclusion: Samples #68, #69 and #70 are all readily distinguishable from background and appear to contain high amounts of DNA, with sample #69 having the highest apparent concentration, reflective of 10× more DNA (i.e. a 3-4 fold lower Ct) than sample #68 which appears to contain the lowest DNA concentration.

B) Testing of Tablet Samples

Protocol: Tablet samples were labeled as sample #71, #72 and #73. Five different tablets were taken from each sample pack and prepared for analysis at the laboratory. Sterile cotton tipped applicators were dipped in deionized water and used to swab one side of each tablet ten times. The tip of the cotton swab was removed and placed into the PCR reaction mixture. The samples were then tested using the MyGo Pro Real-Time PCR (qPCR) Instrument.

Results: Ct (threshold cycle) values were obtained for all reactions and the average of the five sample preparations was calculated for each sample.

Conclusion: All three samples, #71-#73 appear to contain measurable amounts of DNA taggant. DNA was detected in the appropriate powder and tablets samples via qPCR and no DNA was detected in the untagged powder and tablet samples.

The invention claimed is:

1. A method of attaching a nucleic acid to an object for authentication purposes comprising providing a plurality of submicron particles; adding an amount of nucleic acid suspended in a solvent to the submicron particles so that only enough nucleic acid is present to form a monolayer around each submicron particle; extracting the solvent to form a monolayer of nucleic acid covering each submicron particle; and attaching the nucleic acid covered submicron particles to an object to be authenticated using nucleic acid amplification and/or taggant sequence detection techniques for authentication.

2. The method according to claim 1, wherein the nucleic acid is DNA.

3. The method according to claim 1, wherein the submicron particles are metal oxides.

4. The method according to claim 3, wherein the metal oxides are titanium dioxide or silicon dioxide.

5. The method according to claim 1, wherein the solvent is water.

6. The method according to claim 1, wherein the submicron particles are exposed to a substance to optimize the desired level of adhesion of nucleic acid to submicron particle, whereby enough nucleic acid may be recovered from the object to use nucleic acid amplification and/or taggant sequence detection techniques.

7. The method according to claim 6, wherein the substance is sodium phosphate, borate, monopotassium phosphate, vanadate, citrate, ethylenediaminetetraacetic acid, sodium dodecyl sulfate, and sodium lauryl sulfate.

8. A method of authenticating an object comprising providing a plurality of submicron particles; adding an amount of nucleic acid suspended in a solvent to the submicron particles so that only enough nucleic acid is present to form a monolayer around each submicron particle; extracting the solvent to form a monolayer of nucleic acid covering each submicron particle; attaching the nucleic acid covered submicron particles to an object to be authenticated; taking a sample of the object to recover the nucleic acid from the submicron particles; isolating the nucleic acid; amplifying and identifying the nucleic acid using nucleic acid amplification and/or taggant sequence detection techniques; and verifying the authenticity of the object by the presence of the nucleic acid.

9. The method according to claim 8, wherein the nucleic acid is DNA.

10. The method according to claim 8, wherein the submicron particles are metal oxides.

11. The method according to claim 10, wherein the metal oxides are titanium dioxide or silicon dioxide.

12. The method according to claim 8, wherein the solvent is water.

13. The method according to claim 8, wherein the submicron particles are exposed to a substance to optimize the desired level of adhesion of nucleic acid to each submicron particle, whereby enough nucleic acid may be recovered from the object to use nucleic acid amplification and/or taggant sequence detection techniques.

14. The method according to claim 13, wherein the substance is sodium phosphate, borate, monopotassium phosphate, vanadate, citrate, ethylenediaminetetraacetic acid, sodium dodecyl sulfate, and sodium lauryl sulfate.

* * * * *